US00PP36002P2

(12) United States Plant Patent
Carrella

(10) Patent No.: US PP36,002 P2
(45) Date of Patent: Jul. 9, 2024

(54) ***CALIBRACHOA* PLANT NAMED 'KLECA22915'**

(50) Latin Name: ***Calibrachoa* sp.**
Varietal Denomination: KLECA22915

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/224,281

(22) Filed: Jul. 20, 2023

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC . A01H 5/02; A01H 5/00; A01H 6/821; A01H 6/82
See application file for complete search history.

(56) References Cited

PUBLICATIONS

Ball Seed MiniFamous Neo Red Hawaii *Calibrachoa* 2023 retrieved on Oct. 26, 2023 at https://www.ballseed.com/PlantInfo/?phid=066007160051870, one page. (Year: 2023).*
Eason Horticultural Resources 2023 Annual Report (EHR 101) retrieved on Oct. 26, 2023 at https://issuu.com/ehrpublications/docs/ehr_101_-_2023_report, pp. 1,5-6). (Year: 2023).*
Vellekoop. CAST 2023 in 115+ pictures and videos, Floral Daily, retrieved on Oct. 26, 2023 at https://www.floraldaily.com/article/9519239/cast-2023-in-115-pictures-and-videos/, 5 pp. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new *Calibrachoa* plant particularly distinguished by having large red single flowers with yellow stripes and a semi-trailing habit, is disclosed.

1 Drawing Sheet

Genus and species: *Calibrachoa* sp.
Variety denomination: 'KLECA22915'.

BACKGROUND OF THE NEW PLANT

The present invention comprises a new and distinct variety of *Calibrachoa*, botanically known as *Calibrachoa* sp., and hereinafter referred to by the variety name 'KLECA22915'. 'KLECA22915' originated from a controlled-cross between the proprietary female *Calibrachoa* variety 'CA-2018-2630' (unpatented) and the male *Calibrachoa* variety 'CA-2018-3002' (unpatented).

In August 2018, two *Calibrachoa* parental lines, the female variety 'CA-2018-2630' and the male variety 'CA-2018-3002' were crossed via a controlled-cross in Stuttgart, Germany and seeds were obtained. The seeds were sown and plants were grown for evaluation. A plant line was selected in May 2019 and subsequently named 'KLECA22915'. In May 2019, 'KLECA22915' was first vegetatively propagated by cuttings in Stuttgart, Germany. 'KLECA22915' was found to reproduce true to type in successive generations of asexual propagation via cuttings.

SUMMARY

The following are the most outstanding and distinguishing characteristics of this new variety when grown under normal horticultural practices in Stuttgart, Germany.

1. Large, single red flowers with yellow stripes; and
2. Semi-trailing plant habit.

DESCRIPTION OF THE PHOTOGRAPH

This new *Calibrachoa* plant is illustrated by the accompanying photograph which shows a close-up of the whole plant. The photograph is of a 20-week-old-plant grown in in Stuttgart, Germany in August 2022. The colors shown are as true as can be reasonably obtained by conventional photographic procedures.

DESCRIPTION OF THE NEW VARIETY

The following detailed descriptions set forth the distinctive characteristics of 'KLECA22915'. The data which define these characteristics were collected from asexual reproductions carried out in Stuttgart, Germany. Data was collected on 15-week old plants after transplant in Latina, Italy. Color references are to The R.H.S. Colour Chart of The Royal Horticultural Society of London (R.H.S.), 5$^{th}$ edition (2007).

Classification:
*Family.*—Solanaceae.
*Species.*—*Calibrachoa* sp.
*Common name.*—*Calibrachoa.*

Parentage:
*Female.*—*Calibrachoa* line 'CA-2018-2630' (unpatented).
*Male.*—*Calibrachoa* line 'CA-2018-3002' (unpatented).

Plant description:
*Life cycle.*—Annual.
*Form.*—Short lived subshrub.
*Habit.*—Semi-trailing.
*Height* (*from soil line to top of foliage*).—10.5 cm.
*Spread.*—43.0 cm.
Propagation:
*Type cuttings.*—Tip cuttings.
*Time to produce a rooted cutting.*—3 weeks.
Stems:
*Stem color.*—RHS 144B.
*Pubescence.*—Present.
*Pubescence color.*—RHS 155A.
*Stem diameter.*—0.1 cm.
*Stem length.*—From soil line to first node: 1.8 cm. Total length: 28.0 cm.
*Internode length.*—1.7 cm.
Leaves:
*Arrangement.*—Opposite.
*Shape.*—Cuneate.
*Apex.*—Obtuse.
*Base.*—Acute.
*Margin.*—Ciliate.
*Surface.*—Upper surface: RHS 137A. Lower surface: RHS 137C.
*Surface pubescence.*—Present.
*Pubescent color.*—RHS 155A.
*Venation.*—Pinnate.
*Venation color.*—Upper surface: RHS 137B. Lower surface: RHS 137D.
*Length.*—2.9 cm.
*Width.*—1.1 cm.
*Color.*—Upper surface: RHS 137B. Lower surface: RHS 137D.
*Fragrance.*—Absent.
Flowers:
*Flowering habit.*—Single.
*Flower type.*—Single.
*Flowering requirements.*—A minimum amount of sunlight is required.
*Duration of flowers.*—7 days.
*Corolla* (*both surfaces*).—Smooth.
*Shape.*—Funnel form.
*Fragrance.*—Absent.
*Number of flowers per plant.*—150 to 200.
Flower buds (before opening):
*Surface.*—Pubescent.
*Length.*—2.1 cm.
*Diameter.*—0.5 cm.
*Shape.*—Irregular to oblong.
*Color.*—Top buds: RHS 71B. Base buds: RHS 2C.
*Typical number per plant.*—20 to 30.
Petiole:
*Length.*—0.8 cm.
*Diameter.*—Less than 0.1 mm.
*Color.*—RHS 137B.
Peduncle:
*Length.*—3.0 cm.
*Diameter.*—Less than 0.1 cm.
*Color.*—RHS 144B.
*Texture.*—Pubescent.
*Anthocyanin color.*—RHS N79A.
Flower description:
*Flower depth.*—2.3 cm.
*Flower tube length.*—1.7 cm.
*Flower tube diameter.*—0.8 cm.
*Flower diameter.*—3.9 cm.
*Flower throat diameter.*—0.7 cm.
*Pedicel color.*—RHS 144B and RHS N79A.
*Calyx.*—Funnel shaped, salver form.
Sepals:
*Quantity.*—5.
*Shape.*—Obtuse.
*Texture.*—Pubescent.
*Apex.*—Ciliate.
*Margin.*—Ciliate.
*Length.*—0.9 cm.
*Diameter.*—0.2 cm.
*Sepal color.*—Upper surface: RHS 137B. Lower surface: RHS 138A.
Petals:
*Shape.*—Obcordate.
*Quantity.*—5 fused petals.
*Length.*—1.6 cm.
*Apex.*—Obtuse.
*Margin.*—Entire.
*Base.*—Fused into the tube.
*Pubescence.*—Absent.
*Lobe length.*—1.6 cm.
*Lobe width.*—1.2 cm.
*Color* (*the colors in the description refer the color when the flower is fully open; in general there aren't main difference between different status of flowering*).—Lobe color: Upper surface: RHS 61B and RHS 7A (stripes, located on the fused parts of the lobes) area of main color at transition from near base of corolla to corolla very small. Lower surface: RHS 63B and 9C (stripes). Corolla tube color. Inner: RHS 7A. Outer: RHS 9C.
*Fragrance.*—Absent.
*Lobing intensity.*—Medium.
*Vein intensity.*—Weak.
Reproductive organs:
*Stamen number.*—5.
*Stamen color.*—Anther color: RHS 13B. Anther length: 0.1 mm. Filament length: 0.6 cm. Filament color: RHS 157C. Pollen amount: Medium quantity. Pollen color: RHS 12A.
*Ovary.*—Placenta arrangement: Ovate. Pistil number: 1. Pistil length: 0.9 cm. Stigma color: RHS 145B. Stigma shape: Rounded. Style length: 0.8 cm. Style color: RHS 145B.
Fruit/seed set: None observed.
Disease/insect resistance: No pests and disease were observed.

COMPARISON WITH PARENTAL LINES AND KNOWN VARIETY

'KLECA22915' is distinguished from its parents as described in Table 1 and Table 2:

TABLE 1

Comparison with Female Parental Line

| Trait | Variety 'KLECA22915' | Female parent 'CA-2018-2630' |
|---|---|---|
| Flower size | Bigger flower than the female parent | Smaller flower than Variety 'KLECA22915' |

TABLE 2

| Comparison with Male Parental Line | | |
|---|---|---|
| Trait | Variety 'KLECA22915' | Male Parent 'CA-2018-3002' |
| Earliness | 7 days earlier than male parent | Later than Variety 'KLECA22915' |

'KLECA22915' is most similar to the *Calibrachoa* plant named 'KLECA22822' (unpatented). Differences between the two varieties are described in Table 3:

TABLE 3

| Comparison with Similar Variety | | |
|---|---|---|
| Trait | Variety 'KLECA22915' | 'KLECA22822' |
| Flower color | Red color as opposed to blue color of commercial line | Blue color |

I claim:

1. A new and distinct cultivar of *Calibrachoa* Plant Named 'KLECA22915' as described and illustrated herein.

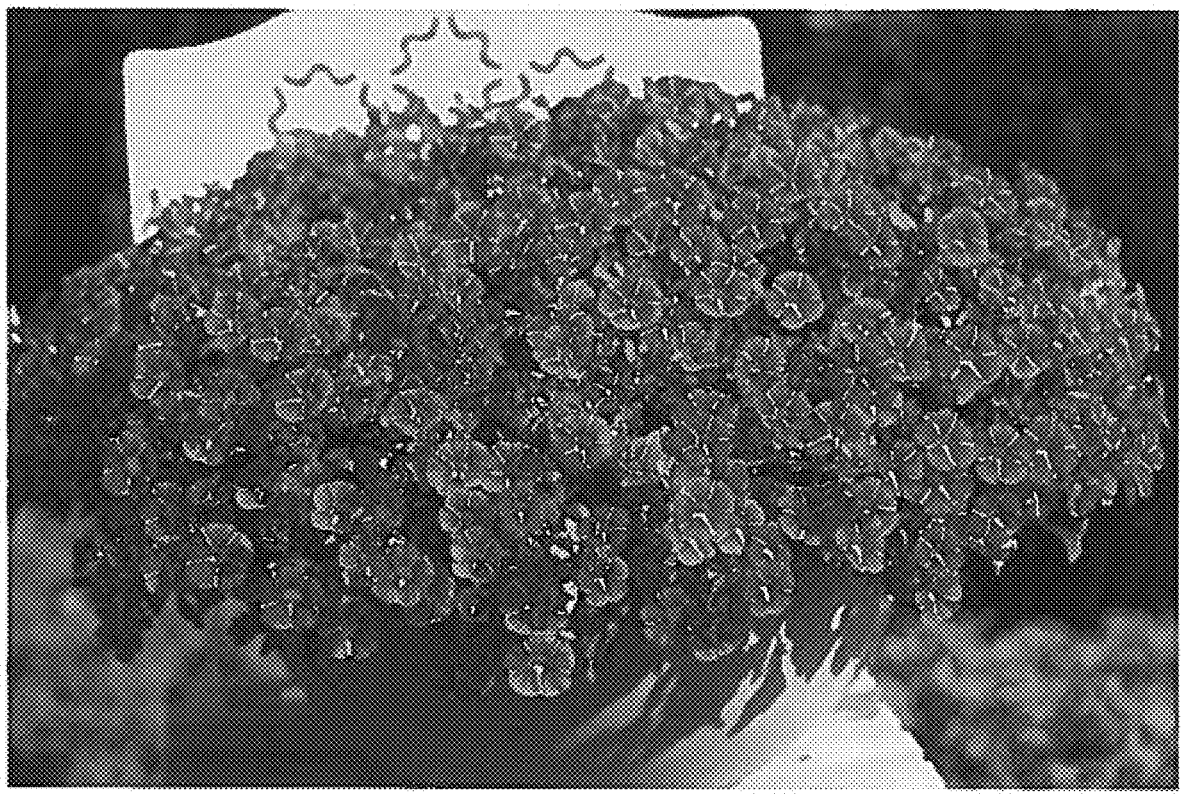

* * * * *